United States Patent [19]
Villain et al.

[11] Patent Number: 5,645,583
[45] Date of Patent: Jul. 8, 1997

[54] INJECTABLE POLYETHYLENE OXIDE GEL IMPLANT AND METHOD FOR PRODUCTION

[75] Inventors: Franck L. Villain, Annecy, France; Jean-Marie A. Parel, Miami Shores; William Gerald Lee, Miami Beach, both of Fla.; Gabriel Simon, Barcelona, Spain

[73] Assignee: University of Miami, Miami, Fla.

[21] Appl. No.: 463,595

[22] Filed: Jun. 5, 1995

Related U.S. Application Data

[63] Continuation of Ser. No. 299,583, Sep. 1, 1994, which is a continuation-in-part of Ser. No. 836,711, Feb. 19, 1992, Pat. No. 5,372,580, which is a continuation-in-part of Ser. No. 551,807, Jul. 12, 1990, Pat. No. 5,090,955.

[51] Int. Cl.⁶ .................................. A61F 2/14; A61F 2/16
[52] U.S. Cl. ........................... 623/5; 623/6; 623/66; 128/898
[58] Field of Search ................. 623/5, 6, 66; 604/21; 606/166, 22; 128/898, DIG. 21

[56] References Cited

U.S. PATENT DOCUMENTS

| | | | |
|---|---|---|---|
| 3,264,202 | 8/1966 | King | 204/159.14 |
| 3,419,006 | 12/1968 | King | 128/268 |
| 4,616,644 | 10/1986 | Saferstein et al. | 128/156 |
| 4,634,558 | 1/1987 | Merger et al. | 260/404 |
| 4,706,680 | 11/1987 | Keusch et al. | 128/640 |
| 4,713,243 | 12/1987 | Schiraldi et al. | 424/151 |
| 4,883,699 | 11/1989 | Aniuk et al. | 428/36.9 |
| 4,911,691 | 8/1990 | Aniuk et al. | 604/164 |

FOREIGN PATENT DOCUMENTS

| | | |
|---|---|---|
| 251744 | 1/1988 | European Pat. Off. . |
| 2707499 | 4/1993 | France . |
| 1117032 | 6/1968 | United Kingdom . |
| 9011719 | 10/1990 | WIPO . |
| 9417851 | 8/1994 | WIPO . |

OTHER PUBLICATIONS

Salassa, "Polyethylene Oxide Gel", Dec., 1991 Arch. Otolaryngol Head Neck Surg., vol. 117.
Cohn & Younes, "Biodegradable PEO/PLA Block Copolymers", 1988, Journal of Biomedical Materials Research.
Graefe's Archive For Clinical and Experimental Optholmology, (1991) 229: 418–424, Gel Injection Adjustable Keratoplasty, Simon et al.

(List continued on next page.)

*Primary Examiner*—David Isabella
*Attorney, Agent, or Firm*—Jerrold J. Litzinger

[57] ABSTRACT

A biocompatible polyethylene oxide gel implant and method for production which can be injected into the human body for tissue replacement and augmentation. The implant is prepared by dissolving a sample of essentially pure polyethylene oxide in a saline solution in a sealed canister, removing all free oxygen from the container and replacing it with an inert gas, such as argon, and irradiating the canister with a gamma ray source to simultaneously crosslink the polyethylene oxide while sterilizing it. The gel can then be placed into a syringe and injected into the body.

4 Claims, 3 Drawing Sheets

OTHER PUBLICATIONS

Archivos de la Sociedad Esponaola De Oftalmologia, (1991) 61:271–282, Technica Quirurgica in vitro Y Adjuste Queratometrico de una Inyeccion de Gel Interlamelar, Simon et al.

Invest. Ophthal Vis Sci. (1990) v. 31 No. 3, p. 301, Gel Injection Adjustable Keratoplasty, Simon et al.

8th Congress of the European Intraocular Implantlens Council Book of Abstracts, (1990);. 122, Gel Injection Adjustable Keratoplasty, Simon et al.

8th Congress of the European Intraocular Implantlens Council, Book of Abstracts (1990), p. 183, Remodeling of the Cornea with Intralamellar Gel Implants Simon et al.

9th Southern Biomedical Engineering Conference, (1990), Biopolymeric Gels and Corneal Curvature, Simon et al.

Invest. Ophthalmol & Vis, Res. (1991) 32(3): In Vivo Evaluation of Gel Injection Adjustable Keratoplasty, Simon et al.

Accommodation Club Recent Advances in Cataract and Corneal Refractive Surgery Symposium (1991): Gel Injection Adjustable Keratoplasty: Short Term In Vivo Evaluation Simon et al.

SPIE vol. 1644 Ophthalmie Technologies II (1992) 329: Gel Injection Adjustable Keratoplasty–Short Term In Vivo Evaluation & Histopathology Simon et al.

Genie Biologique et Biomateriaux en Ophtalmologie (1992): Gel Injection Adjustable Keratoplasty Etude In Vivo, Simon et al.

Arvo, (1993): Long Term In Vivo Topographic Studies of Gel Injection Adjustable Keratoplasty, Simon et al.

Arvo (1993): Soft Tissue Augmentation by a New Polymer, Parel et al.

3rd American–International Congress on Cataract, Iol and Refractive Surgery (May 1993): Long Term In Vivo Study of Gel Injection Adjustable Keratoplasty, Simon et al.

Arvo, (1993): Histopthological Study of Synthetic Annular Keratophakia, Simon et al.

Arvo, (1993): Long Term In Vivo Topographic Studies of Gel Injection Adjustable Keratoplasty, Simon et al.

Bordeaux Sympossium International of Ophthalmology, (Sep. 1993): Gel Injection Adjustable Keratoplasty Long–Term In Vivo Topographic Studies, Simon et al.

J. Fr. Ophtalmol. (1994)17(2) p. 83–92: Les Resultats de 2 ans D.'Experimentation Animale Anneaux Intrastromaux en Polyoxyde D'Ethylene Reticule, Simon et al.

Invest Ophthalmol & Vis Res, v. 35(4);. 2024 (1994): Long Term Clinical and Histological Results of Gel Injection Adjustable Keratoplasty in the Cat, Simon et al.

Invest. Ophth. & Vis Res, v. 35(4) p. 2024 (1994): Mathematical Model of Gel Injection Adjustable Keratoplasty, Parel et al.

INJECTABLE POLYETHYLENE OXIDE GEL IMPLANT AND METHOD FOR PRODUCTION

REFERENCE TO RELATED APPLICATION

This application is a continuation of application Ser. No. 08/299,583, filed Sep. 1, 1994, which was a continuation-in-part of U.S. Ser. No. 07/836,711, filed Feb. 19, 1992, now U.S. Pat. No. 5,372,580, which was a continuation-in-part of U.S. Ser. No. 07/551,807, filed Jul. 12, 1990, which is now U.S. Pat. No. 5,090,955.

BACKGROUND OF THE INVENTION

This invention relates generally to a method for producing a polyethylene oxide implant and, in particular, to a method for producing a biocompatible crosslinked polyethylene oxide gel which can be injected into the human body for tissue replacement and augmentation.

It is well known that hydrogels have been used in many biomedical applications, as they can be made non-toxic and compatible with tissue. U.S. Pat. Nos. 4,983,181 and 4,994,081, which issued in 1991 to Civerchia, teach a method of polymerizing a hydrogel in the presence of a crosslinking agent to form a three dimensional polymeric meshwork having controlled spacings between the molecules thereof to anchor the macromolecules which have a known size and to insure that the micromolecules will be substantially uniformly interspersed within the polymeric meshwork of the polymerized hydrophilic monomer. The step of forming the crosslinking of the hydrogel can be performed with a crosslinking agent which may be external, such as ultraviolet radiation, or a crosslinking agent added to the hydrogel clear viscous monomer solution, which crosslinking agent may be, for example, ethyleneglycol dimethacrylate. The hydrogel taught in these patents is a transparent collagen hydrogel which is capable of promoting epithelial cell growth.

Some of the drawbacks of using collagen gels are that they typically biodegrade in three to six months, and are well known for their infectious and immunologic reactions. In addition, collagen implants are, in time, colonized by the recipient cells and vessels.

Another type of substance commonly used in biomedical applications is a silicone gel. However, silicone gels are also known to cause immunologic reactions, and tend to migrate away from the implantation site. In addition, silicone implants become encapsulated by dense fibrous tissues created by cellular reactions to a foreign substance implanted into the tissue. Finally, while silicone gels do allow for efficient oxygen diffusion, there is insufficient transportation of nutrients across the space that the implants occupy.

SUMMARY OF THE PRESENT INVENTION

It is therefore an object of the present invention to provide a process for producing a gel implant which is biocompatible with and nonerodible in the body.

Another object of the present invention is to provide an implant which can be easily removed from the body if desired.

It is also an object of the present invention to provide a biocompatible gel which is injectable into the body and does not cause infectious, inflammatory, or immunologic reactions following implantation.

It is a further object of the present invention to provide an injectable biocompatible gel which does not migrate away from the site of the injection, and allows for both oxygen and nutrient support.

It is a still further object of the present invention to provide a polyethylene oxide gel which can be cracked after gelation but before entering the body or during the actual injection process.

These and other objects are accomplished in the present instance by using a novel process for creating a polyethylene oxide (PEO) gel which can be injected into the body as an implant. Using gamma radiation crosslinking, a PEO gel in deoxygenated saline solution is synthesized for use as permanent soft implants for tissue replacement and augmentation, which is useful in plastic and reconstructive surgery, ophthalmic procedures such as refractive corneal surgery, retinal detachment surgery, and oculoplastics.

Using this novel process, the PEO gel is biocompatible and its characteristics can be engineered by modulating PEO-water concentration and radiation dosage (to control its transparency and hardness) and by modulating electrolyte concentration (to control volume expansion and final water content) to fit a specific medical requirement. The gel is injectable through small gauge (e.g. 25 ga) needles, and is found biocompatible intrastromally and subcutaneously. The gel is not colonized by cells and vessels, and is therefore easily removable by flushing using saline solutions (preferably hypertonic). The shape of implants composed of this PEO gel is moldable by digital massage of the tissue surrounding the implant.

DETAILED DESCRIPTION OF THE PREFERRED EMBODIMENT

Polyethylene oxide (PEO) and polyethylene glycol (PEG) are fabricated by two different methods, but generally refer to the same polymeric synthetic product having the formula:

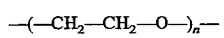

$$-(-CH_2-CH_2-O-)_n-$$

The difference between these two polymers resides in their respective molecular weight usage. PEGs have molecular weight below a few thousand daltons, whereas PEOs have molecular weights starting from several thousands to several million daltons.

PEO is soluble in benzene, freon, chloroform, and tetrohydrofurane, and is also soluble in water at all temperatures except near the boiling point. PEO is also soluble in salt solutions.

Figure 1:
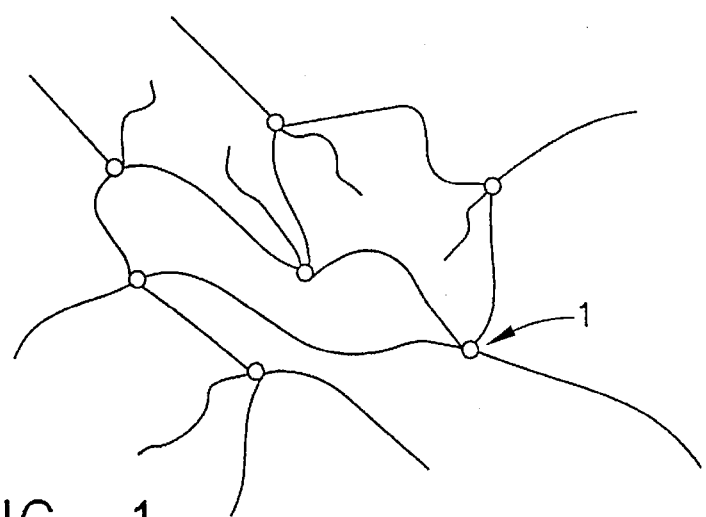
FIG. 1 illustrates pictorially a single PEO molecule.

As the PEO polymer is highly soluble in water, to use it as a biocompatible material, it is necessary to decrease its solubility. This can be done by creating an insoluble crosslinked network, as can be seen in FIG. 1. Each crosslink is indicated by a junction, as shown at 1 in FIG. 1. This network has the advantage to be hydrophilic, and, consequently, it will swell in water.

One method for producing crosslinked PEO is by endlinking the network with a chemical reaction by using, for example, hexamethylene diisocyanate as the crosslinking agent and a branching agent such as mannitol, pentaerythrytol or 1,2,6-hexametriol. However, because toxic chemical reagents (in the same concentration range as PEO) are used during the crosslinking, an additional purification step must be employed to eliminate any remaining trace of the reagents.

Another way to create this network is to expose the PEO to gamma radiation. However, while pure PEO can be gamma ray crosslinked without water, the process requires a very high radiation dosage (greater than 100 Mrad), making it impractical. By using a PEO-water solution, the crosslinking can be accomplished using a much smaller radiation dosage (about 1 Mrad). This crosslinking is indirect and involves water molecules:

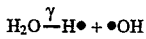

The radicals produced react on the PEO polymer chain to yield:

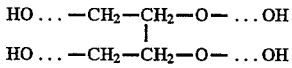

The crosslinked PEO chain has a much higher molecular weight than the base PEO used in the reaction. If a single link occurs between two 200,000 dalton chains a 400,000 dalton molecule is obtained. A link can occur between any two carbon moieties of any two different PEO molecules as shown in the above formula. Gelation occurs when there is at least one crosslink per polymer chain initially present.

Figure 2:
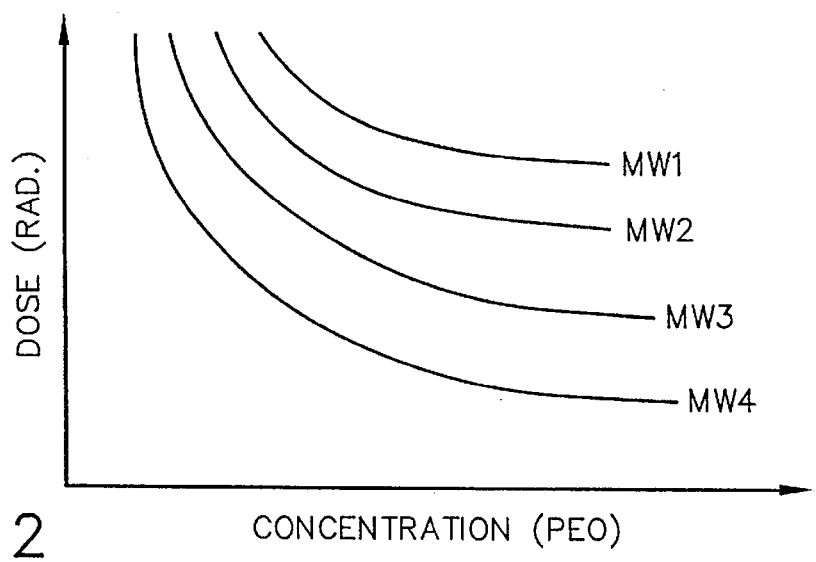
FIG. 2 is a graphic representation showing the influence of molecular weight on gelification dose.

Gelation depends on several parameters: the PEO concentration, the molecular weight, and the radiation dose. The influence can be represented in the chart shown in FIG. 2 showing the radiation dose vs. the PEO concentration in aqueous solution for different molecular weights, where MW1>MW2>MW3>MW4. As can be seen in FIG. 2, at a given concentration, the higher the molecular weight, the lower the radiation dose necessary to form a gel. However, gelation may not occur, as oxygen dissolved in the solution acts as a scavenger of gamma rays and thus will quench the crosslinking process.

To prevent this, the PEO solution should be carefully degassed. The solution is pulled under vacuum until no more bubbles of gas appear in the solution, then the vacuum is replaced by argon or another inert gas. This procedure may be repeated several times in order to decrease the residual amount of oxygen remaining in the solution.

In the preferred embodiment, a 0.8% to 8% PEO solution by weight was prepared by dissolving a PEO preparation (e.g. 200,000 daltons) in a saline solution. The solution used, a Balanced Salt Solution (BSS), was selected as it is best suited for the intended medical application. Other solutions may be used, depending on the intended use of the gel. The BSS composition, which may be obtained from Alcon, Inc., is listed below in Table I.

TABLE I

| Solute | Percentage (by weight) |
|---|---|
| Sodium Chloride | 0.64 |
| Potassium Chloride | 0.075 |
| Calcium Chloride | 0.048 |
| Magnesium Chloride | 0.03 |
| Sodium Acetate | 0.039 |
| Sodium Citrate Dihydrate | 0.17 |

Free oxygen was then removed from the solution by placing the solution in a sealed container which was evacuated using vacuum and then filled with pure Argon gas (>99.999%) to prevent gaseous contamination from the surrounding atmosphere. The canister was then irradiated by exposing it to a gamma ray source (Cobalt 60) for a dosage of between 2.5 and 25 Mrads to crosslink the PEO. To obtain a uniform gel (Isotrope) the solution can be continuously agitated, even during radiation (using a rocking platform oscillatory shaker). Aseptic and contamination-free transfer of the PEO gel to sterile syringes was performed in a laminar flow-hood presterilized with UV radiation for use in experimental procedures which will be discussed.

It was observed that the PEO hydrogel of a specific electrolyte concentration, will swell when immersed in a saline solution with a lower electrolyte content, while it will shrink if immersed in a saline solution with a higher electrolyte concentration. Therefore, implanting a PEO gel crosslinked in a saline solution having a different electrolyte concentration than surrounding tissue will result in a postoperative change of the implant's volume. While this phenomenon may result in postoperative complications in certain medical applications, it can be advantageous in applications such as vitreous substitution with polymers and retinal detachment surgery where controlled tissue-to-tissue compression is required.

For a given PEO solute concentration, the higher the irradiation dosage, the higher the crosslink density. Using a 0.8% PEO solution, the irradiation dosage was varied from 0.8 Mrads to over 13 Mrads. 0.8 Mrads seemed to be the minimum dosage required to obtain gelation without gravitational collapse of the polymer, while any dosage above 9 Mrads seemed to have little effect on the physical properties of the PEO.

A minimal dose of 2.5 Mrad was selected for the irradiation dosage, as it corresponds to the minimum dosage required for gamma ray sterilization. By using a higher dosage, it is possible to simultaneously crosslink and sterilize the PEO gel implant.

Referring again to FIG. 2, it can be seen that for a given crosslink density, the higher the PEO solute concentration, the lower the irradiation dose required. Initial testing performed with a PEO of approximately 200,000 daltons indicated that, below 0.5%, gelation is difficult to obtain, even at a high irradiation dosage. Thus, a solute concentration varying between 0.8% and 8.0% was selected.

With a 0.8% 200,000 dalton PEO solution irradiated at 5 Mrads, the crosslinked gel is transparent and can be used in ophthalmology for corneal tissue augmentation procedures such as Gel Injection Adjustable Keratoplasty (GIAK), which is described in U.S. Pat. No. 5,090,955, which is assigned to the same assignee of the present invention and is hereby incorporated by reference.

Figure 3:
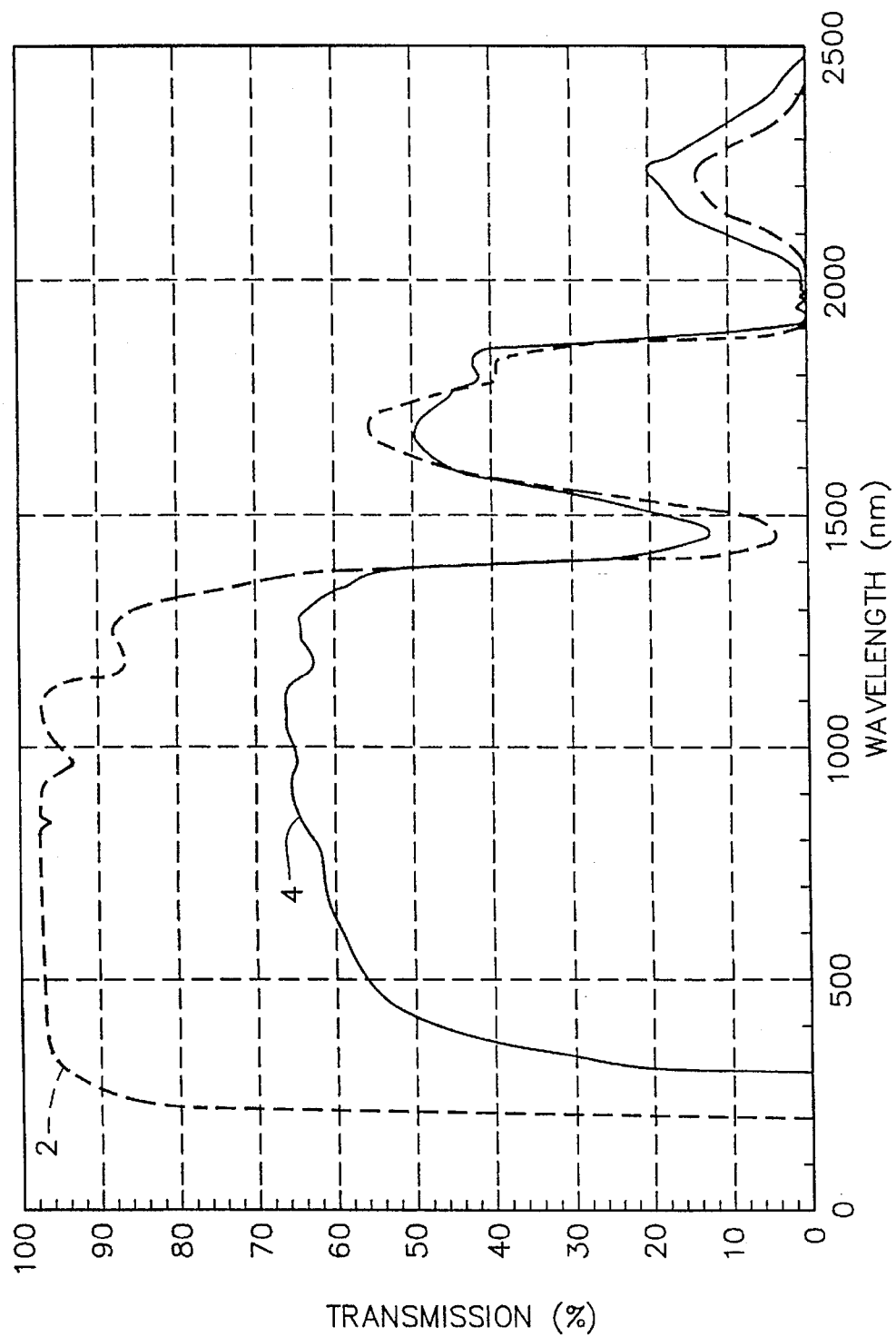
FIG. 3 is a graphic representation showing the percentage of light transmission through both a human cornea and a PEO gel implant prepared by a the present process to the wavelength of light.

Visibility of the gel within the eye is a cosmetic and therapeutic concern related to the GIAK procedure. Gel visibility is related directly to both the reflectivity and absorbance properties of the gel used. Thus, at any visible wavelength, the percentage of transmission of light through the implant should be at least as great as that through the cornea. FIG. 3 shows a graph which illustrates light transmission through both a cornea and an implant prepared according to the present invention as a percentage of transmission of light through the cornea as a function of the wavelength of the light. The graph of light transmission through the gel is a dotted line designated as 2, while the graph of light transmission through the cornea is a solid line designated as 4. As can be seen in FIG. 3, for the visible light spectrum (from 400 nanometers to 800 nanometers) the percentage of light transmission through the gel approaches 100 percent. Therefore, the implant of the present invention is optically transparent to light passing through the implant. FIG. 3 also shows that the implant transmits more light in the near ultraviolet, visible and near infrared range than the normal cornea (wavelengths of 300 to 1350 nm).

Figure 4A:
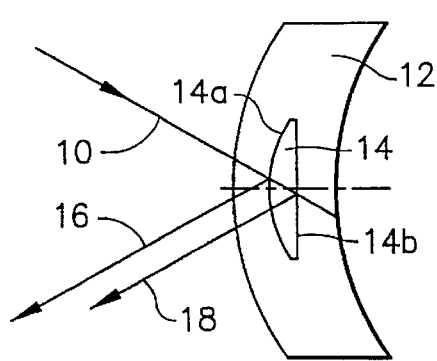
FIGS. 4A and 4B illustrate pictorially the reflection of light from an implant within a cornea.

As the eye can detect approximately 10% difference in reflection, it is important that the index of refraction of the gel differs no more than ±10% from the index of refraction of the cornea. FIG. 4A shows a beam of light passing through an implant which has been placed within the cornea of an eye. A beam 10 passes through the anterior section of cornea 12 and strikes the anterior surface 14a of implant 14, where it is partially reflected as shown at 16. As beam 10 continues through implant 14, it strikes the posterior surface 14b of implant 14, and is partially reflected as shown at 18.

Figure 4B:
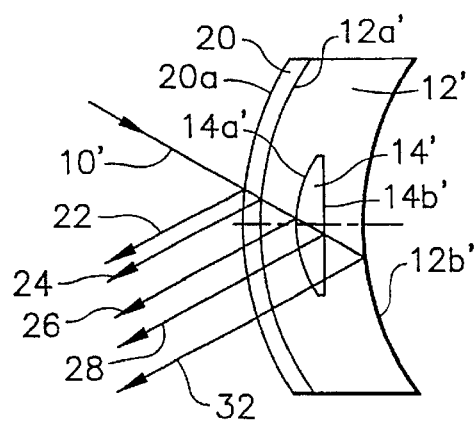

Referring now to FIG. 4B, the reflection properties of the cornea are taken into consideration unless a beam passes through a cornea containing an implant. As beam 10' strikes the anterior surface 20a of the tear film 20 of cornea 12', it is partially reflected, as shown at 22. Beam 10' continues through tear film 20 and is partially reflected at anterior surface 12a' of cornea 12', as shown at 24. Beam 10' continues into cornea 12' where it is partially reflected at anterior surface 14a' of implant 14', as shown at 26. The posterior surface 14b' partially reflects beam 10' as it passes through posterior surface 14b', which is shown at 28. Finally, beam 10' is reflected as it strikes the posterior surface 12b' of cornea 12', as is shown at 32.

Figure 5:
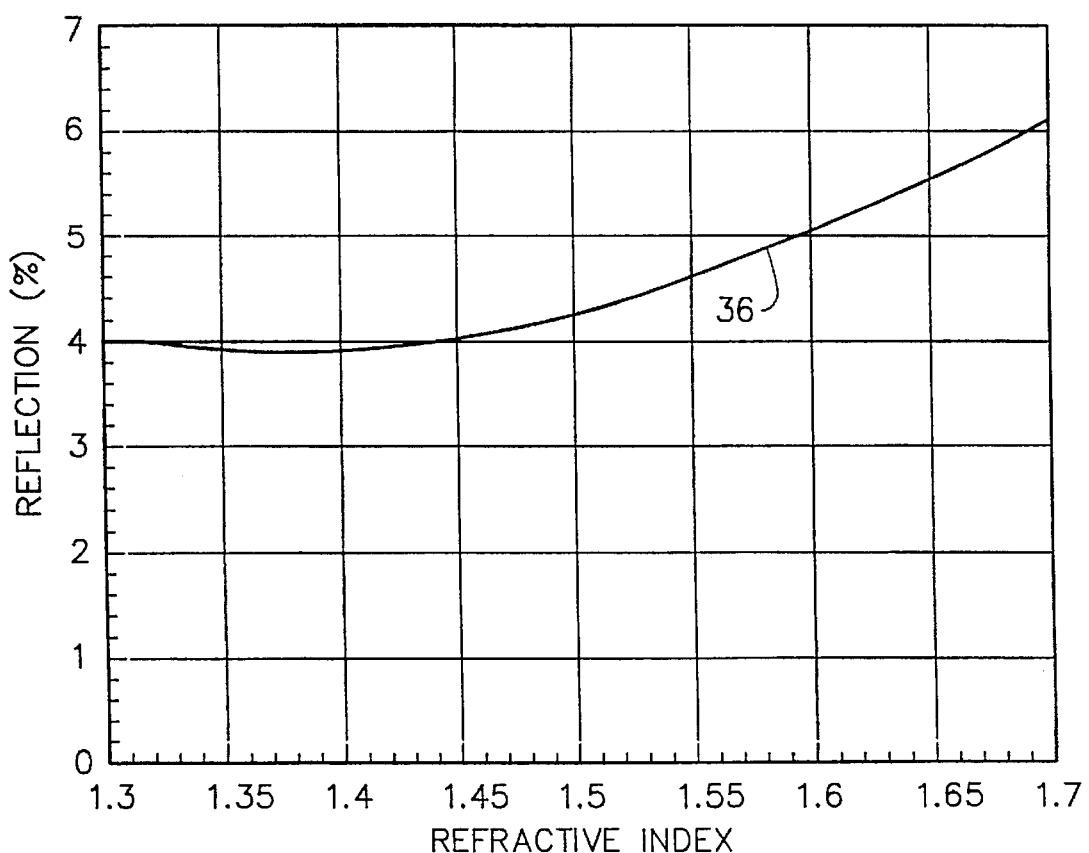
FIG. 5 is a graphic representation showing the percentage of light reflection from a cornea with an implant in relation to the refractive index of the implant.

FIG. 5 illustrates the percentage of light reflected as a function of the refractive index of the implant produced using the method of the present invention. The curve designated at 36 shows the percentage of light reflected by the cornea and implant together as a function of the index of refraction of the implant. As can be seen from FIG. 5, if the index of refraction of the implant equals the index of refraction of the cornea (i.e., 1.376), the percentage of incident light that is reflected is at the minimum, which is approximately 4%. As it is desirable that the total reflection of the cornea and implant together will not differ from the total reflection of the cornea alone by more than approximately 10%, the total reflection of the implant plus cornea should be no greater than 4.4%. If we find the point on line 36 that gives a total reflection of 4.4% it can be seen that it corresponds to an index of refraction for the implant of approximately 1.52. Since a hydrogel is mostly water and the index of refraction of water is approximately 1.3, the index of refraction of the implant should be at least 1.3.

Therefore it is most desirable for the gel to be used in GIAK surgery to have an index of refraction greater than 1.3 and less than 1.52.

It is also essential that the absorbance of the injected gel closely match the absorbance of the cornea. This will be important if it becomes necessary to perform later procedures on the eye. If the gel has different absorbance characteristics, laser ocular surgery and photocoagulation may not be possible, as the light energy will not have a uniform effect on the gel and the cornea.

Figure 6:
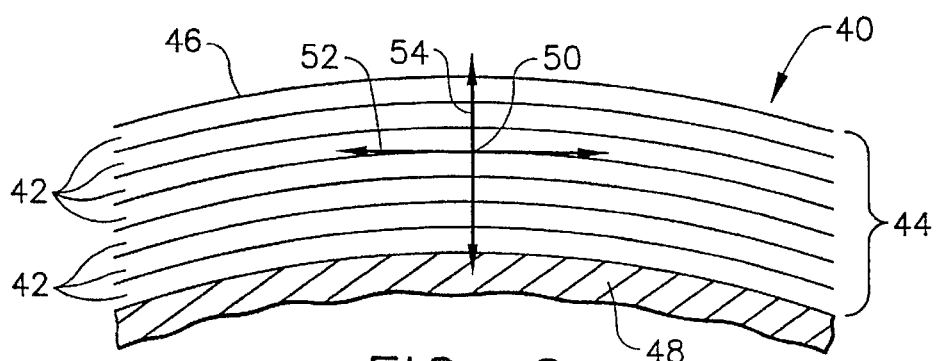
FIG. 6 is a diagrammatic view of the cornea, illustrating both the transverse and radial directions in which the modulus of elasticity is measured.

Another important characteristic of the injected gel that will affect its performance in the eye is its modulus of elasticity. This subject is discussed in an article entitled "Keratoprosthesis: Engineering and Safety Assessment", which was published in the May/June 1993 issue of *Refractive and Corneal Surgery*. If the injected implant is stiffer than the cornea, it will deform the cornea, while if the cornea is stiffer than the implant, it will deform the implant. For example, a keratoprosthesis which is composed of glass or polymethylmethacrylate (PMMA) is subject to extrusion from cornea, as these relatively hard materials have an elastic modulus much greater than that of the cornea. Therefore, to prevent extrusion of the gel from the cornea, its modulus of elasticity must be less than that of the cornea. FIG. 6 shows a representation of a cornea for the purpose of locating the site for selecting the proper modulus of elasticity in both the transverse and radial directions. Cornea 40 is composed of a plurality of layers or lamellae 42 which form the stroma 44. The corneal surface is indicated at 46, while the anterior chamber of the eye is indicated at 48. At the incision site in the cornea for this procedure (approximately 2.5 mm from the corneal center), the thickness of the cornea is between 550 and 650 microns. At the level at which the annular channel is formed which is indicated at 50 in FIG. 6, the cornea has both a radial elastic modulus and a transverse elastic modulus. The radial modulus is directed along a plane designated by 52 while the transverse modulus is directed along a plane designated by 54. The transverse modulus is between $2.19 \times 10^4$ and $4.12 \times 10^4$ newtons/m$^2$, while the radial modulus is between $2 \times 10^6$ and $5 \times 10^6$ newtons/m$^2$. In order to avoid any problems with extrusion, the gel should have an elastic modulus less than both the radial and the transverse moduli of the cornea.

Other necessary characteristics of an injectable gel for this procedure include: the prevention of cell migration into the implant which would impair its removal (if necessary to readjust corneal curvature); and the transmission of oxygen and other essential nutrients through the gel into all parts of the eye.

In an experiment using the procedure taught in the aforementioned patent the sterile crosslinked gel was injected into an annular intrastromal channel formed between the lamellar layers in the cornea of a rabbit at a distance spaced away from the central corneal region. After the channel was formed in the cornea, the gel was injected into the channel using a 19–25 gauge needle. The PEO gel was shown to be non-toxic to the rabbit cornea with an excellent corneal transparency, no surface opacification, no extrusion and no migration. Histologically, no giant cells, no necrosis, and a normal keratocyte population near the implant were found. In addition, the PEO gel was optically transparent in the visible spectrum and its index of refraction (1.334) was relatively close to the corneal refraction index (1.376). The modulus of elasticity of the gel was estimated with a penetrometer at $1.7 \times 10^3$ newtons/m$^2$. It has been shown that gel produced by the method of the present invention remains stable over 22 months in the rabbit cornea. By using a solution during preparation of the PEO gel that approximates the electrolyte concentration or osmotic activity of the cornea, it would be possible to minimize any change in volume of the implant.

Other potential uses are for vitreous substitution and keratophakia lenticules. Increasing the PEO concentration increases the gel mechanical strength while decreasing transparency. For example, a 1% PEO solution irradiated at 5 Mrads will produce a tougher gel which can be used for subcutaneous tissue augmentation procedures performed in plastic and reconstruction surgery, oculoplasty, or other procedures where transparency is not necessary. Several experiments have been conducted in vivo to demonstrate the biocompatibility of this PEO gel when injected subcutaneously. Six rabbits received subcutaneous injection of a PEO gel prepared according to the present invention in the dorsal area and in the ears. The results showed a good tolerance of this material and no apparent degradation of the product after two months.

The gamma ray crosslinking process of PEO solutions produces an excess amount of free water (syneresis). The water may be unwanted in certain surgeries and has to be removed before transferring the gel from the canister to the syringe. To accomplish this task, the canister was equipped with a second chamber separated from the first by a fine mesh screen. After the irradiation procedure, the canister was inverted and the excess water drained into the lower container, while maintaining the crosslinked PEO in a sterile atmosphere.

In certain instances, it may be difficult to predict at the time of manufacture of the PEO what exact shape and size is necessary for a particular implant. In these situations, the PEO gel can be broken into smaller pieces (i.e. cracked) with an average particle size ranging from several microns (for use in filling a biological space with great precision) to over 1 cm for instances in which large volumes of gel are required. The cracking process may be done prior to the implantation or during the implantation process.

While the invention has been shown and described in terms of a preferred embodiment thereof, it will be understood that this invention is not limited to this particular embodiment and that many changes and modifications may be made without departing from the true spirit and scope of the invention as defined in the appended claims.

What is claimed is:

1. A method of implanting a biocompatible gel into the cornea of a mammal, comprising the steps of:

dissolving a sample of polyethylene oxide in a saline solution;

transferring the polyethylene oxide solution to a sealed canister;

removing the free oxygen from said canister;

replacing the oxygen within said canister with an inert gas;

irradiating said canister to crosslink the polyethylene oxide to form a sterile biocompatible gel;

inserting said sterile gel into a syringe;

and implanting said sterile gel into a cornea to form a space filling implant.

2. The method of claim 1, whereas the implanting step causes said sterile gel to crack as it is expelled from said syringe.

3. The method of claim 2, wherein the polyethylene oxide has a molecular weight of at least 200,000 daltons before cross-linking.

4. The method of claim 3, wherein the saline solution comprises a Balanced Salt Solution, and said canister is irradiated by a gamma ray source at a dosage of from 2.5 to 25 Mrads.

* * * * *